United States Patent
Enomoto

(10) Patent No.: US 8,459,869 B2
(45) Date of Patent: Jun. 11, 2013

(54) RADIATION DETECTION DEVICE, IMAGING CONTROL DEVICE, RADIATION IMAGING SYSTEM, AND SELF DIAGNOSTIC METHOD OF RADIATION DETECTION DEVICE

(75) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 244 days.

(21) Appl. No.: 12/923,217

(22) Filed: Sep. 9, 2010

(65) Prior Publication Data

US 2011/0075811 A1    Mar. 31, 2011

(30) Foreign Application Priority Data

Sep. 25, 2009   (JP) ................. 2009-220290

(51) Int. Cl.
*G01D 18/00*   (2006.01)
(52) U.S. Cl.
USPC .................... 378/207; 378/117; 378/98.8
(58) Field of Classification Search
USPC ........................ 378/207, 98.8, 117
See application file for complete search history.

(56) References Cited

U.S. PATENT DOCUMENTS

| | | | | |
|---|---|---|---|---|
| 4,178,510 | A | * 12/1979 | Wagner | ............ 378/51 |
| 4,551,800 | A | * 11/1985 | Riederer et al. | ............ 378/98.12 |
| 7,514,703 | B2 | 4/2009 | Iwakiri | |
| 2004/0062342 | A1* | 4/2004 | Cahill | ............ 378/4 |
| 2006/0002631 | A1* | 1/2006 | Fu et al. | ............ 382/128 |
| 2006/0239415 | A1* | 10/2006 | Liu et al. | ............ 378/207 |

FOREIGN PATENT DOCUMENTS

| | | |
|---|---|---|
| JP | 2001-008198 | 1/2001 |
| JP | 2005-177379 | 7/2005 |
| JP | 2006-047077 | 2/2006 |

* cited by examiner

*Primary Examiner* — Glen Kao
(74) *Attorney, Agent, or Firm* — Jean C. Edwards, Esq.; Edwards Neils PLLC

(57) ABSTRACT

In a cassette-type X-ray detection device, an X-ray detector and a self diagnostic circuit are contained in a cassette casing. When the cassette-type X-ray detection device gets a shock, the self diagnostic circuit is actuated. The self diagnostic circuit reads out from the X-ray detector an offset image being a dark current image, and analyzes the offset image. The self diagnostic circuit finds out an abnormal portion from the offset image, and diagnoses whether the X-ray detector is available, unavailable, or partly available based on the size and position of the abnormal portion. Shock detection and a diagnostic result are displayed on a touch panel provided in the cassette casing, and sent to a console device via a communication unit.

11 Claims, 13 Drawing Sheets

FIG. 4
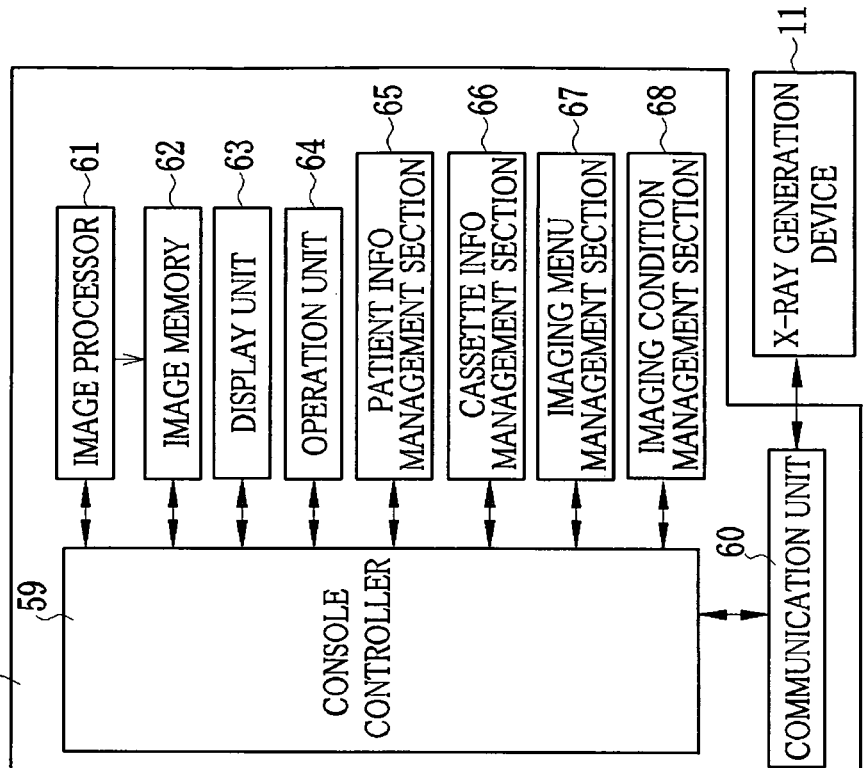
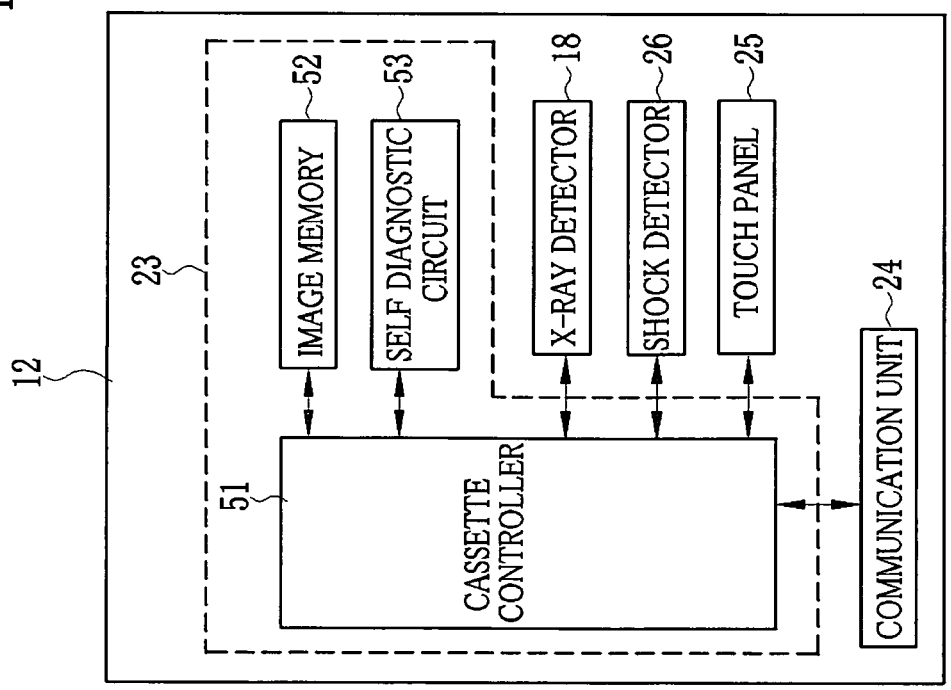

RADIATION DETECTION DEVICE, IMAGING CONTROL DEVICE, RADIATION IMAGING SYSTEM, AND SELF DIAGNOSTIC METHOD OF RADIATION DETECTION DEVICE

CROSS-REFERENCE TO RELATED APPLICATIONS

The present application claims priority from Japanese Patent Application No. 2009-220290, filed Sep. 25, 2009, the contents of which are herein incorporated by reference in their entirety.

BACKGROUND OF THE INVENTION

1. Field of the Invention

The present invention relates to a radiation detection device having a radiation detector such as a flat panel detector contained in a cassette casing, and a radiation imaging apparatus including this radiation detection device, a consol device, and the like.

2. Description Related to the Prior Art

In a medical field, a radiation imaging apparatus for diagnostic imaging, e.g. an X-ray imaging apparatus that uses an X-ray as a radiation is widely known. The X-ray imaging apparatus is constituted of an X-ray generation device for applying an X-ray beam to a patient's body part to be examined, and an X-ray detection device for detecting the X-ray beam that has passed through the patient's body part. As the X-ray detection device, a cassette containing an imaging plate (IP) instead of an X-ray film, and a flat panel detector (FPD) are used in recent years. The IP has photostimulable storage phosphors for storing received radiation levels, and an X-ray image is produced by reading the IP with a specific laser scanner. The FPD, on the other hand, converts the received X-ray beam into signal charges, and produces the X-ray image in real time. Furthermore, a cassette-type FPD, in which the FPD is contained in a casing of the same shape and size as those of the cassette of the X-ray film or the IP, is recently developed so that the cassette-type FPD is loaded on the conventional X-ray imaging apparatus, instead of the X-ray film cassette.

The cassette-type FPD is frequently carried about because of being shared among a plurality of X-ray imaging apparatuses, or often moved with the portable X-ray imaging apparatus for use in radiography in a consulting room or a sick room. The frequent carriage increases the possibility of a break of the FPD by dropping or bumping the cassette-type FPD during the carriage.

To prevent use of the broken cassette-type FPD, for example, according to Japanese Patent Laid-Open Publication No. 2005-177379, the cassette-type FPD has a shock detection circuit and a self diagnostic circuit. In this cassette-type FPD, when the shock detection circuit detects a shock, the self diagnostic circuit is actuated to detect the presence of a failure. Also, in U.S. Pat. No. 7,514,703, the cassette-type FPD has an accelerometer. When the accelerometer detects an abnormal acceleration, electric power feeding to every part is stopped.

In the Japanese Patent Laid-Open Publication No. 2005-177379, the self diagnostic circuit diagnoses whether or not the cassette-type FPD is workable. However, even if the cassette-type FPD is workable, the image quality of the X-ray image is sometimes degraded to a level insufficient for a medical diagnosis. The self diagnosis cannot ensure the image quality of the X-ray image. In the U.S. Pat. No. 7,514,703, the cassette-type FPD stops feeding the electric power based on only the acceleration. Thus, whether or not the cassette-type FPD is broken, the FPD become unusable.

Furthermore, since the FPD is expensive, few medical institutions keep the extra cassette-type FPD on hand. Therefore, even if the cassette-type FPD is partly damaged, it is desirable to temporarily use the partly damaged cassette-type FPD as long as it can produce the X-ray image adequate for the medical diagnosis.

SUMMARY OF THE INVENTION

An object of the present invention is to provide a radiation detection device, an imaging control device, a radiation imaging system, and a self diagnostic method of the radiation detection device that self-diagnose a failure of a radiation detector, and inform a radiologic technologist of an available part of the radiation detector if the radiation detector is partly damaged.

To achieve the above and other objects, a radiation detection device according to the present invention includes a radiation detector, a shock detector, a self diagnostic circuit, and a cassette casing for containing the radiation detector, the shock detector, and the self diagnostic circuit. The radiation detector has a plurality of pixels that convert a radiation into signal charges and accumulate the signal charges. The signal charges accumulated in the individual pixels during an entry of the radiation are read out as an image signal of a radiographic image. The shock detector detects a shock given to the radiation detector. The self diagnostic circuit analyzes an offset image in response to detection of the shock by the shock detector to diagnose whether or not the radiation detector is available. The offset image is formed from the signal charges accumulated in the individual pixels of the radiation detector after the shock detection without the entry of the radiation.

It is preferable that the self diagnostic circuit analyzes the offset image, and finds out an abnormal portion in the offset image, and diagnoses whether or not the radiation detector is available based on the size or position of the abnormal portion.

The self diagnostic circuit may analyze at least one of a pixel value, a noise level, a point defect, and a line defect of the offset image.

If the offset image has no abnormal portion, the self diagnostic circuit diagnoses that the radiation detector is available. If the abnormal portion occupies a whole surface of the offset image or is positioned in a middle of the offset image, the self diagnostic circuit diagnoses that the radiation detector is unavailable. If the abnormal portion is positioned at an end portion of the offset image, the self diagnostic circuit diagnoses that the radiation detector is partly available.

The radiation detection device may further include a display unit for displaying the shock detection and a diagnostic result. When the radiation detector is unavailable or partly available, the display unit may carry out display operation, if a magnitude of the shock is a shock threshold value or more, or the number of times the shock is detected is a detection number threshold value or more.

The radiation detection device may further include a sending unit for sending the shock detection and the diagnostic result, or the shock detection and the offset image to outside. When the radiation detector is unavailable or partly available, the sending unit may carry out sending operation, if the magnitude of the shock is the shock threshold value or more, or the number of times the shock is detected is the detection number threshold value or more.

An imaging control device for controlling a radiation detection device according to the present invention includes a receiving unit and a controller. The receiving unit receives the shock detection and the diagnostic result from the sending unit. The controller permits or bans use of the radiation detection device in accordance with the diagnostic result.

The controller permits the use of the radiation detection device, if the diagnostic result indicates that the radiation detection device is available or partly available. The controller bans the use of the radiation detection device, if the diagnostic result indicates that the radiation detection device is unavailable.

The imaging control device may further include a display unit for indicating a usable area of the radiation detection device, if the radiation detection device is diagnosed to be partly available.

The imaging control device may further include an imaging menu management section for switching display of an imaging menu to choose a body part to be imaged in accordance with the diagnostic result.

The imaging menu management section may make all body parts to be imaged choosable, if the radiation detection device is diagnosed to be available. The imaging menu management section may change the choosable body part to be imaged in accordance with the usable area, if the radiation detection device is diagnosed to be partly available.

The imaging control device may further include a cassette information management section and a substitute proposing section. The cassette information management section stores and manages information of a plurality of radiation detection devices. If one of the radiation detection devices is diagnosed to be unavailable or partly available, the substitute proposing section proposes use of another one of the radiation detection devices the information of which is stored in the cassette information management section.

A radiation imaging system according to the present invention includes a radiation generation device for applying a radiation to an object, a radiation detection device, and an imaging control device for controlling the radiation generation device and the radiation detection device. The radiation detection device includes a radiation detector, a shock detector, a self diagnostic circuit, and a portable cassette casing. The radiation detector has a plurality of pixels for converting the radiation into the signal charges and accumulating the signal charges. The signal charges accumulated in the individual pixels during an entry of the radiation are read out as an image signal of a radiographic image. The shock detector detects a shock that is given to the radiation detector. The self diagnostic circuit analyzes the offset image in response to the shock detection by the shock detector to diagnose whether or not the radiation detector is available. The cassette casing contains the radiation detector, the shock detector, and the self diagnostic circuit.

The imaging control system may further include a maintenance device. The maintenance device has a judgment function and a communication unit. The judgment function precisely judges from the offset image whether or not the radiation detector is available. The communication unit sends the offset image and a judgment result to the radiation detection device or the imaging control device.

A self diagnostic method of the radiation detection device according to the present invention includes the steps of detecting the shock given to the radiation detection device; just after detection of the shock, reading out as the offset image the signal charges accumulated in the individual pixels of the radiation detection device without the entry of the radiation; and analyzing the offset image, and diagnosing whether or not the radiation detection device is available.

The diagnosing step may include the steps of analyzing the offset image and finding out the abnormal portion occurring in the offset image; and diagnosing whether or not the radiation detection device is available based on the size or position of the abnormal portion.

In the diagnosing step, if the offset image has no abnormal portion, the radiation detection device may be diagnosed to be available. If the abnormal portion occupies the whole surface of the offset image or is positioned in the middle of the offset image, the radiation detection device may be diagnosed to be unavailable. If the abnormal portion is positioned at the end portion of the offset image, the radiation detection device may be diagnosed to be partly available.

According to the present invention, whether the radiation detector is available, partly available, or unavailable is diagnosed based on the size or position of the abnormal portion occurring in the offset image. Thus, it is possible to certainly grasp a state of damage to the radiation detector. Even if apart of the radiation detector is damaged, radiography is smoothly carried out with use of a usable area, which works properly.

BRIEF DESCRIPTION OF THE DRAWINGS

For more complete understanding of the present invention, and the advantage thereof, reference is now made to the following descriptions taken in conjunction with the accompanying drawings, in which:

FIG. 4 is a block diagram of the X-ray imaging apparatus according to a first embodiment;

DESCRIPTION OF THE PREFERRED EMBODIMENTS

First Embodiment

Figure 1:
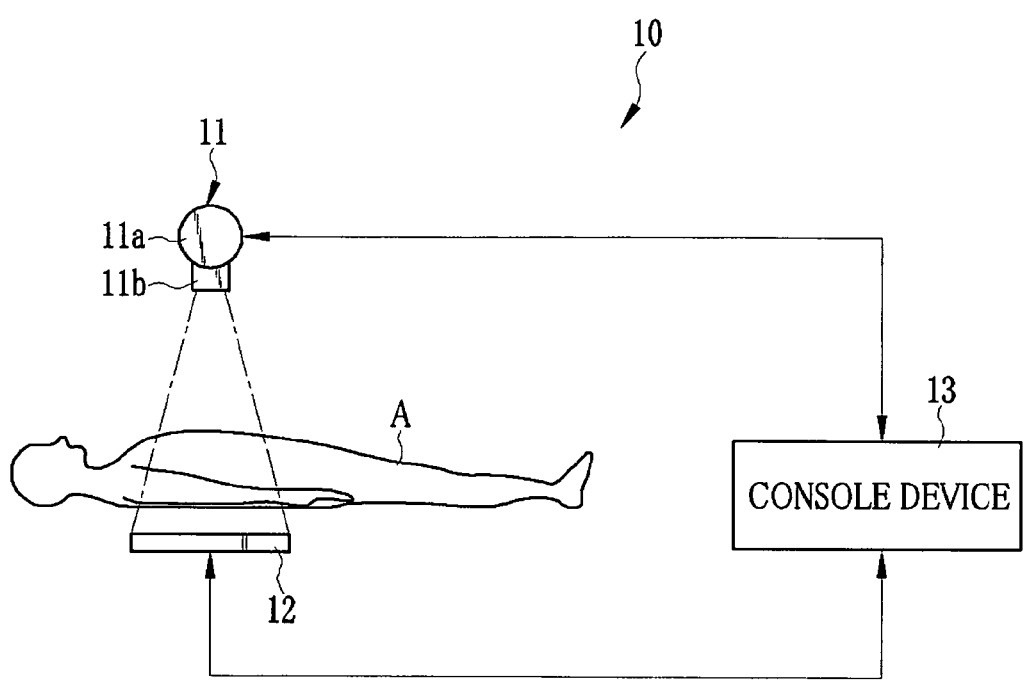
FIG. 1 is a schematic view of an X-ray imaging apparatus.

As shown in FIG. 1, an X-ray imaging apparatus 10 is constituted of an X-ray generation device 11 that applies an X-ray beam (shown by alternate long and short dash lines in FIG. 1) to a patient's body A, a cassette-type X-ray detection device (hereinafter simply called cassette) 12 that receives the X-ray beam having passed through the patient's body A, and a consol device 13 that controls the X-ray generation device 11 and the cassette 12. The X-ray generation device 11 and the cassette 12 are set up inside a radiation shielded chamber or a radiation room, and the console device 13 is set up outside the radiation shielded chamber.

The X-ray generation device 11 is constituted of an X-ray tube 11a for generating the X-ray beam, and a collimator 11b for limiting an irradiation field of the X-ray beam. The X-ray generation device 11 is movably supported by a support member. The X-ray generation device 11 is disposed so as to face the cassette 12, and the irradiation field of the X-ray beam is variable in accordance with a patient's body part to be examined, which is chosen from the console device 13.

Figure 2:
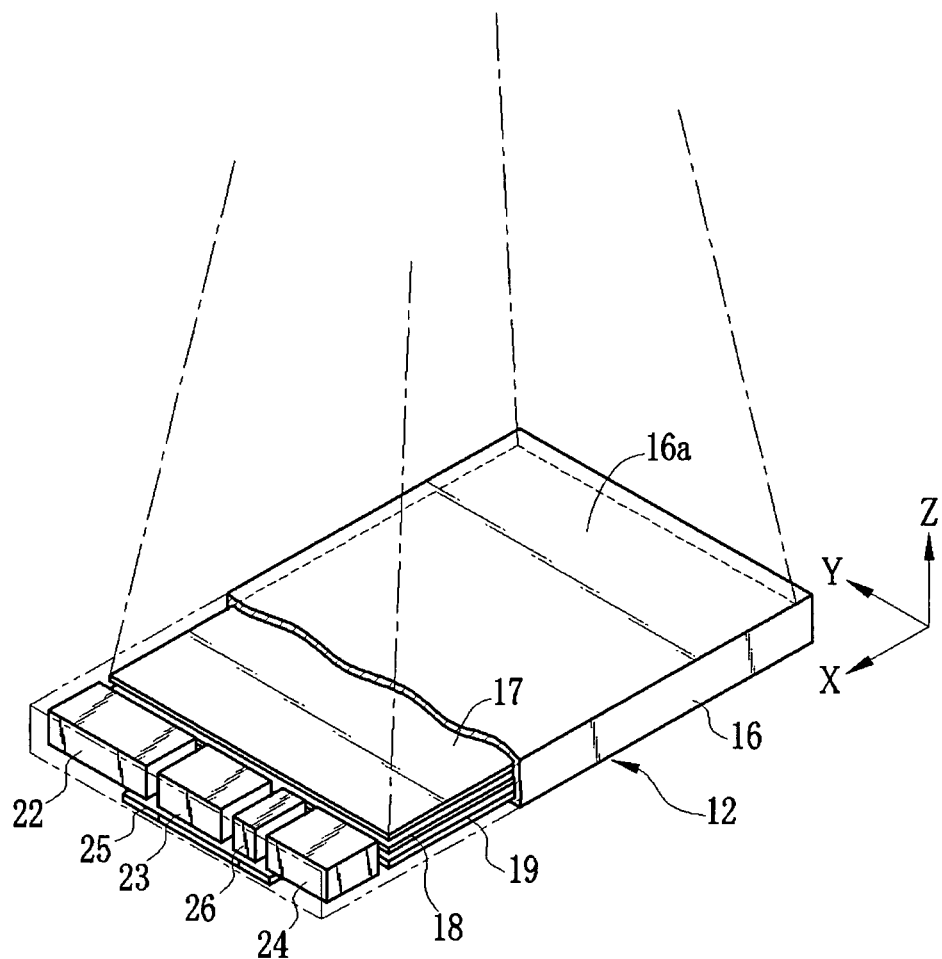
FIG. 2 is a perspective view of a cassette-type X-ray detection device.

Referring to FIG. 2, the cassette 12 has the same shape and size as those of a conventional IP cassette, and is detachably loaded on an X-ray table or the like. As a matter of course, radiography is sometimes carried out with the cassette 12 making contact with the patient's body A. The cassette 12 is shared among a plurality of X-ray imaging apparatuses, and is sometimes brought out of the radiation shielded chamber together with the portable X-ray imaging apparatus for use in the radiography in a consulting room, a sickroom, or the like.

The cassette 12 is provided with a cassette casing 16 made of an X-ray transparent material. Inside the cassette casing 16, a grid 17, an X-ray detector 18, and a lead plate 19 are disposed in this order from a side of an incident surface 16a of the cassette casing 16. The grid 17 removes X-rays scattered from the patient's body A. The X-ray detector 18 detects the X-ray beam that has passed through the body part to be examined. The lead plate 19 absorbs the X-rays scattered backward.

The cassette casing 16 also contains a power source 22, a control unit 23, a communication unit 24, a touch panel 25, and a shock detector 26. The power source 22 feeds electric power to each part of the cassette 12. The control unit 23 controls operation of the X-ray detector 18. The communication unit 24 communicates with the console device 13 by radio in order to send and receive various types of data including image data. The touch panel 25 is disposed on a surface opposite to the incident surface 16a to display various setting items and messages.

The shock detector 26 is composed of a triaxial accelerometer, for example, and detects and measures acceleration, inclination, shock, and the like applied to the cassette 12. in triaxial directions along X, Y, and Z axes. Thus, it is detectable on which part the cassette 12 has fallen or bumped, and the magnitude of the shock due to the fall or bump. Although the fall or bump of the cassette 12 tends to occur while the cassette 12 is carried about, the cassette 12 is generally turned off during the carriage. Thus, the sock detector 26 is preferably supplied with the electric power and activated, even while the cassette 12 is turned off.

Figure 3:
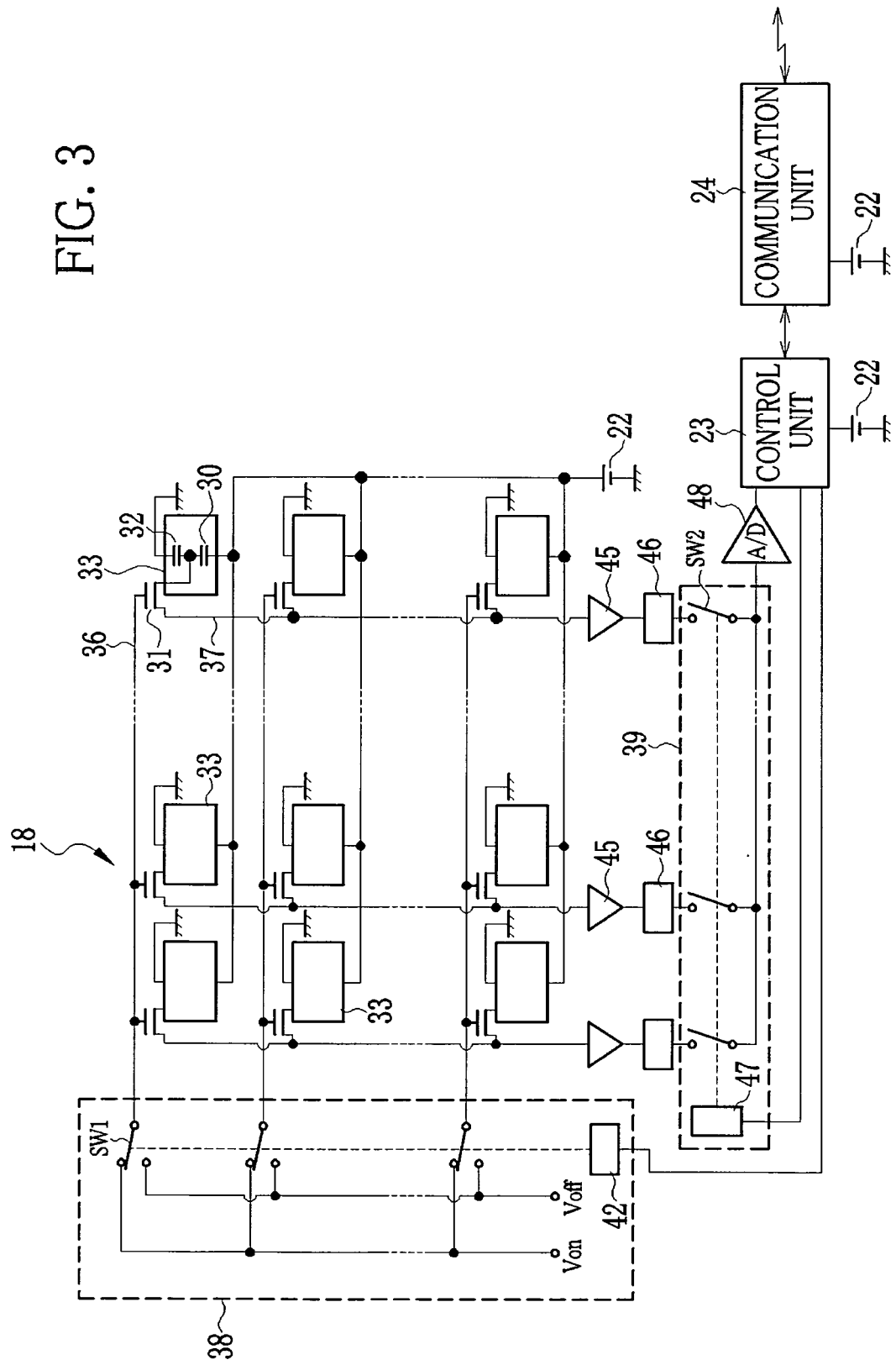
FIG. 3 is a circuit diagram of the X-ray detection device.

As shown in FIG. 3, the X-ray detector 18 is constituted of an array of thin film transistors (TFTs) 31, and photoelectric conversion layers 30 disposed on each TFT 31. The photoelectric conversion layer 30 is made of amorphous selenium (a-Se), and converts the received X-rays into an electric charge. The electric charge generated by the photoelectric conversion layer 30 is accumulated in a capacitor 32. Then, upon turning on the TFTs 31 on a row basis, the electric charges are read from the capacitors 32 as an X-ray image. In FIG. 3, the connection between a single pixel 33 having the photoelectric conversion layer 30 and the capacitor 32 and the single TFT 31 is illustrated, though an illustration of the other pixels 33 is omitted.

A source of each TFT 31 is connected to the pixel 33. A gate of each TFT 31 is connected to a gate line 36 extending in a row direction, and a drain of each TFT 31 is connected to a signal line 37 extending in a column direction. The gate lines 36 are connected to a line scanning driver 38. The signal lines 37 are connected to a multiplexer 39, which composes a readout circuit.

To each gate line 36, the line scanning driver 38 applies a control voltage $V_{on}/V_{off}$ to turn on or off the TFTs 31 aligned in the row direction. In this case, the line scanning driver 38 is provided with a plurality of switches SW1 for switching the control voltage applied to each gate line 36 between $V_{on}$ and $V_{off}$, and address decoder 42 that outputs a selection signal for selecting one of the plurality of switches SW1. To the address decoder 42, the control unit 23 supplies an address signal.

When the application of the control voltage $V_{on}$ turns on the TFTs 31 in the single row, the electric charges accumulated in the capacitors 32 of the pixels 33 in that row flow into the signal lines 37. The electric charges read through the individual signal lines 37 are amplified by amplifiers 45. The amplifiers 45 are connected to the multiplexer 39 through sample holding circuits 46. The multiplexer 39 has a plurality of switches SW2 for switching among the signal lines 37, and an address decoder 47 that outputs a selection signal for selecting one of the plurality of switches SW2. To the address decoder 47, the control unit 23 supplies an address signal. The multiplexer 39 is connected to an analog-to-digital converter (A/D) 48. Accordingly, digital-format image data that is converted by the A/D 48 is supplied to the control unit 23.

As shown in FIG. 4, the control unit 23 of the cassette 12 is provided with a cassette controller 51, an image memory 52, and a self diagnostic circuit 53. The cassette controller 51, which overall controls each part of the cassette 12, includes a CPU for carrying out various computing processes, a ROM for storing control programs executed by the CPU, a RAM for temporarily storing various types of data, and the like. The image memory 52 stores the image data outputted from the X-ray detector 18.

In response to detection of the acceleration or the shock by the shock detector 26, the self diagnostic circuit 53 reads from the X-ray detector 18 an offset image that is formed after the shock, and diagnoses whether the cassette 12 is available, partly available, or unavailable based on the offset image. The offset image is an image formed from signal charges accumulated by a dark current or the like in the capacitors 32 of the individual pixels 33 shown in FIG. 3 while no X-ray is detected. Analyzing the offset image allows determination of the presence or absence of damage to the pixels 33 and the like.

The self diagnostic circuit 53 analyzes the offset image, and identifies from an analysis result an abnormal portion of the offset image, that is, a portion different from a corresponding portion of the offset image obtained by the normal pixels 33. The self diagnostic circuit 53 judges that the pixel 33 corresponding to the abnormal portion is damaged. In the analysis of the offset image, at least one of a pixel value, a noise level, a point defect, and a line defect is inspected, for example.

As for the analysis of the pixel value (also called QL value) of the offset image, every pixel value is checked to find out the pixel having the abnormal pixel value. Each pixel value should be stable, because the offset image is produced from the signal charges accumulated by the dark current of the X-ray detector 18. Thus, finding out the pixel having the abnormal pixel value in the offset image allows determination of the damaged pixel 33.

Figure 5:
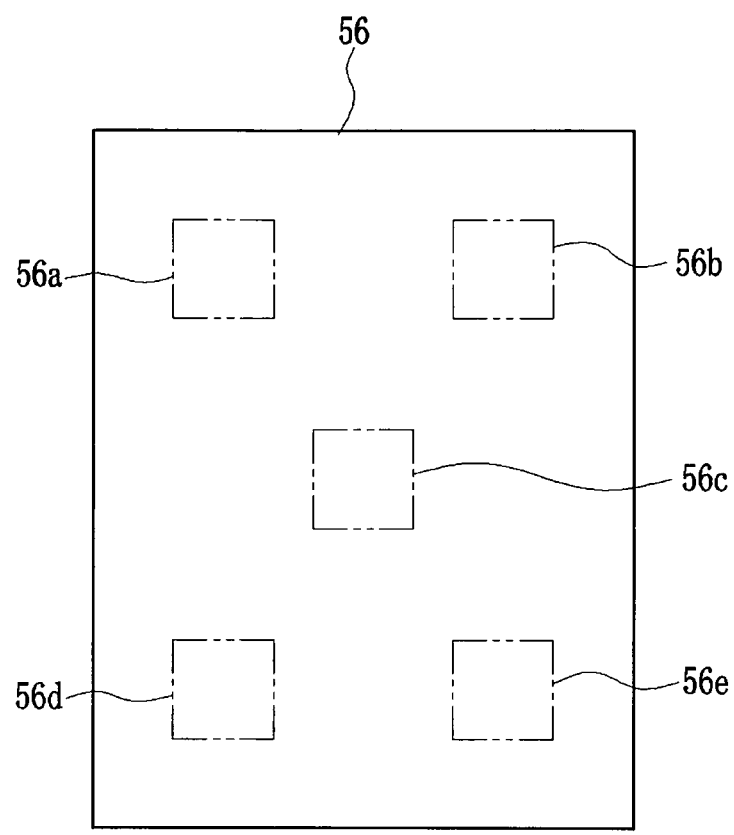
FIG. 5 is an explanatory view showing an example of an offset image.

As for the analysis of the noise level of the offset image, as shown in FIG. 5, a root mean square value of density variations is calculated in each of measurement areas 56a to 56e located in, for example, four quadrants and the middle of an offset image 56, to obtain an RMS granularity. Then, the RMS granularity of each of the measurement areas 56a to 56e is compared with a reference value, and is checked whether or not to be within a predetermined range. This analysis allows determination of whether or not the X-ray detector 18 can perform the radiography with the specified RMS granularity, and an area of the X-ray detector 18 that can perform the radiography with the specified RMS granularity.

As for the analysis of the point defect and the line defect, a point-shaped defect and a line-shaped defect are detected from the offset image. This detection result is compared with a latest defect map stored in advance, so as to confirm whether or not the number of the point defects or the line defects is abruptly increased in comparison with that of the defect map. The pixels 33 corresponding to the abruptly increased point defects or line defects are judged to be damaged. Since the X-ray detector 18 has a lot of pixels 33, the point defect in which only one pixel has sensitivity different from that of the other pixels, and the line defect in which the all aligned pixels have abnormal sensitivity tend to occur. Thus, the X-ray detector 18 creates and stores the defect map, which indicates the position and the size of the point defect and the line defect, not only during manufacture but also at regular time intervals, in order to correct the point defect and the line defect of the X-ray image based on the defect map. This defect map is used in the analysis of the point defect and the line defect of the offset image.

When the cassette 12 is registered on the console device 13, the self diagnostic circuit 53 takes and stores the latest defect map created by the consol device 13, and compares with the defect map the point defect and the line defect detected in the offset image. This analysis allows determination of breakage of each pixel 33 in the X-ray detector 18. The detection of the point defect and the line defect is also described in Japanese Patent Laid-Open Publication Nos. 2001-008198 and 2006-047077, for example.

In the analysis of the offset image, at least one of items including the pixel value, the noise level, the point defect, and the line defect is inspected, and an appropriate combination of the items or all of the items may be inspected. If the plurality of items are inspected, it is preferable to determine the abnormal portion of the offset image in accordance with general judgment of analysis results.

The self diagnostic circuit 53 judges that the X-ray detector 18 is available, if there is no abnormal portion in the offset image 56. The self diagnostic circuit 53 judges that the X-ray detector 18 is unavailable, if the abnormal portion occupies the whole surface of the offset image 56, or does not exist at an end portion of the offset image 56 because a usable area becomes narrow. The self diagnostic circuit 53 judges that the X-ray detector 18 is partly available, if the abnormal portion exists at the end portion of the offset image 56. In a case where the X-ray detector 18 is judged to be partly available, the self diagnostic circuit 53 identifies the usable area thereof.

The shock detector 26 sends the shock detection to the cassette controller 51, and the self diagnostic circuit 53 sends a diagnostic result to the cassette controller 51. The cassette controller 51 displays the shock detection and the diagnostic result on the touch panel 25, and sends the shock detection and the diagnostic result to the consol .device 13 via the communication unit 24.

As shown in FIG. 4, the console device 13 is provided with a console controller 59, a communication unit 60, an image processor 61, an image memory 62, a display unit 63, an operation unit 64, a patient information management section 65, a cassette information management section 66, an imaging menu management section 67, an imaging condition management section 68, and the like.

The console controller 59, as with the cassette controller 51, is composed of a CPU for carrying out computing processes, a ROM for storing control programs and control data, a RAM for temporarily storing various types of data, and the like, and overall controls every part of the console device 13. The communication unit 60 sends and receives necessary information including the image data to and from the communication unit 24 and the X-ray generation device 11 by wired or wireless communication.

The image processor 61 applies various types of image processing to the image data received from the cassette 12. The image memory 62 stores the image data after the image processing. The display unit 63 includes a monitor such as an LCD, and a display circuit for displaying the X-ray image, various operation screens such as an imaging menu, and the like. The operation unit 64 includes a keyboard, a mouse, and the like, and is used in various settings and operations. The operation unit 64 includes an exposure button. Upon pushing the exposure button, the X-ray beam is emitted from the X-ray generation device 11, and the cassette 12 is actuated to capture the X-ray image.

The patient information management section 65 manages patients' information. The patients' information includes a name, a sex, an ID number, and the like of each patient, and is information to identify each patient. The cassette information management section 66 manages cassette information of each cassette 12 registered on the console device 13. The cassette information includes an ID number of the cassette 12, X-ray image correction data including the defect map obtained by calibration, and the diagnostic result by the self diagnostic circuit 53. The console controller 59 refers to the cassette information before using the cassette 12. If the cassette 12 is judged to be unavailable by the self diagnosis, the console controller 59 bans use of the cassette 12.

The imaging menu management section 67 switches the imaging menu displayed on the display unit 63, based on the diagnostic result registered on the cassette information management section 66. The imaging menu is a menu for choosing the patient's body part to be examined among a head, a spine, a chest/abdomen, an arm, and a leg, for example.

Figure 6:
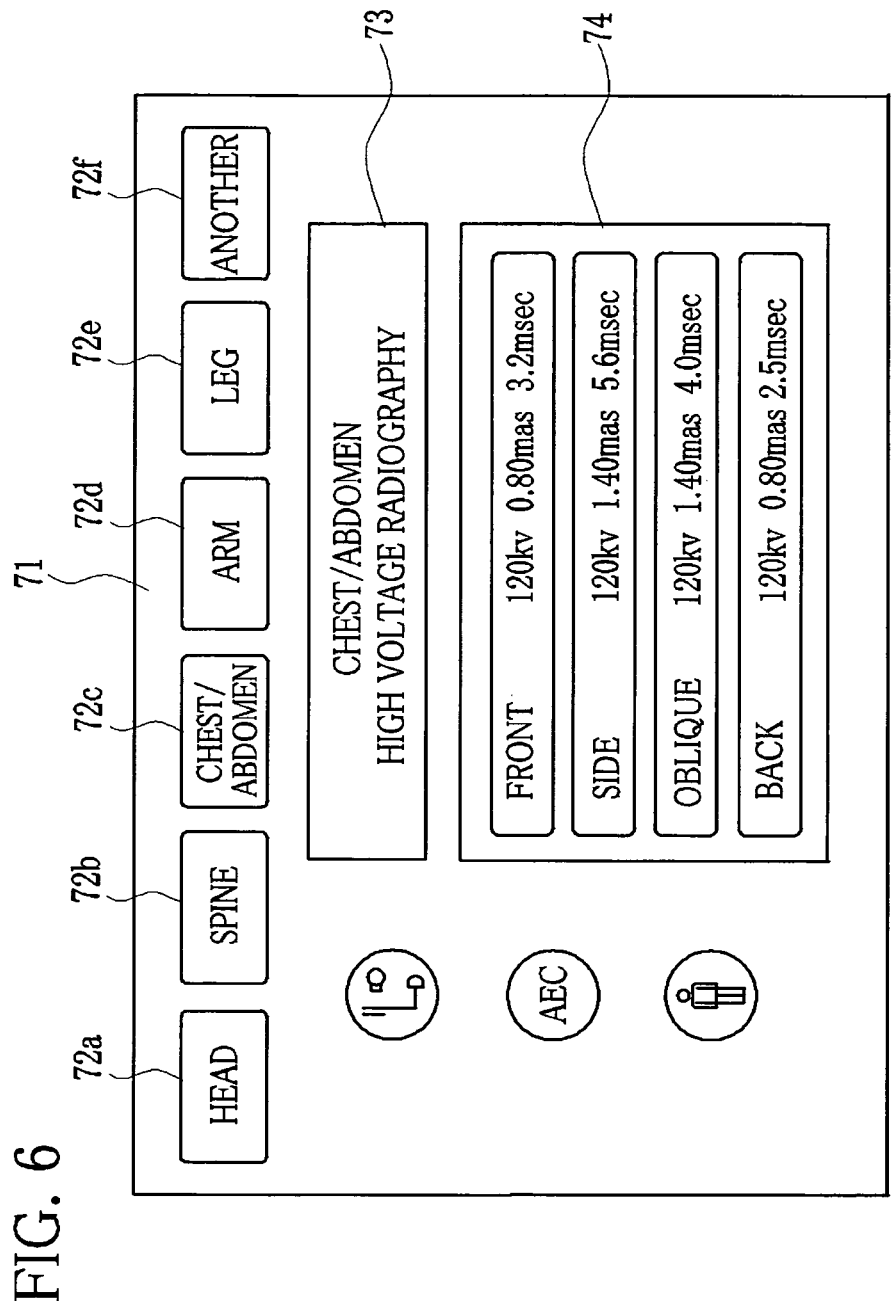
FIG. 6 is an explanatory view showing an example of a normal imaging menu displayed on a monitor.

If the cassette 12 is judged to be available by the self diagnosis, the imaging menu management section 67 displays a normal imaging menu 71 on the display unit 63, as shown in FIG. 6. This normal imaging menu 71 has choice buttons 72a to 72f from which every body part to be examined is choosable, and a choice box 73 for indicating the chosen body part to be examined, a submenu box 74 for choosing the direction of imaging the chosen body part to be examined, and the like.

Figure 7:
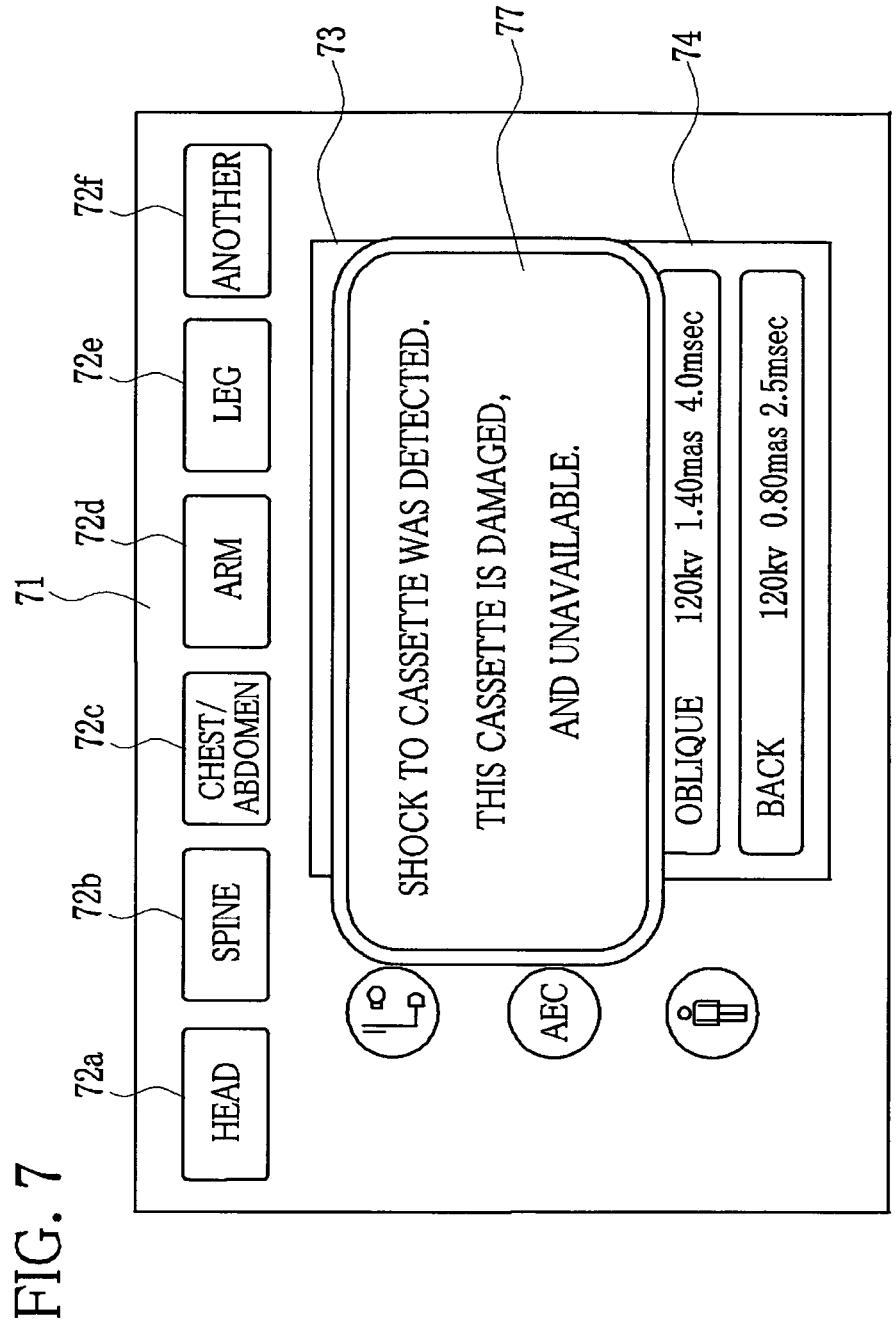
FIG. 7 is an explanatory view showing an example of an unavailability message displayed on the monitor.

If the cassette 12 is judge to be unavailable by the self diagnosis, the imaging menu management section 67 displays a message box 77 over the normal imaging menu 71, as shown in FIG. 7. The message box 77 says that the cassette 12 got a shock, and the shock damaged the cassette 12 and made the cassette 12 unavailable. At this time, operation on the normal imaging menu is preferably banned.

Figure 8:
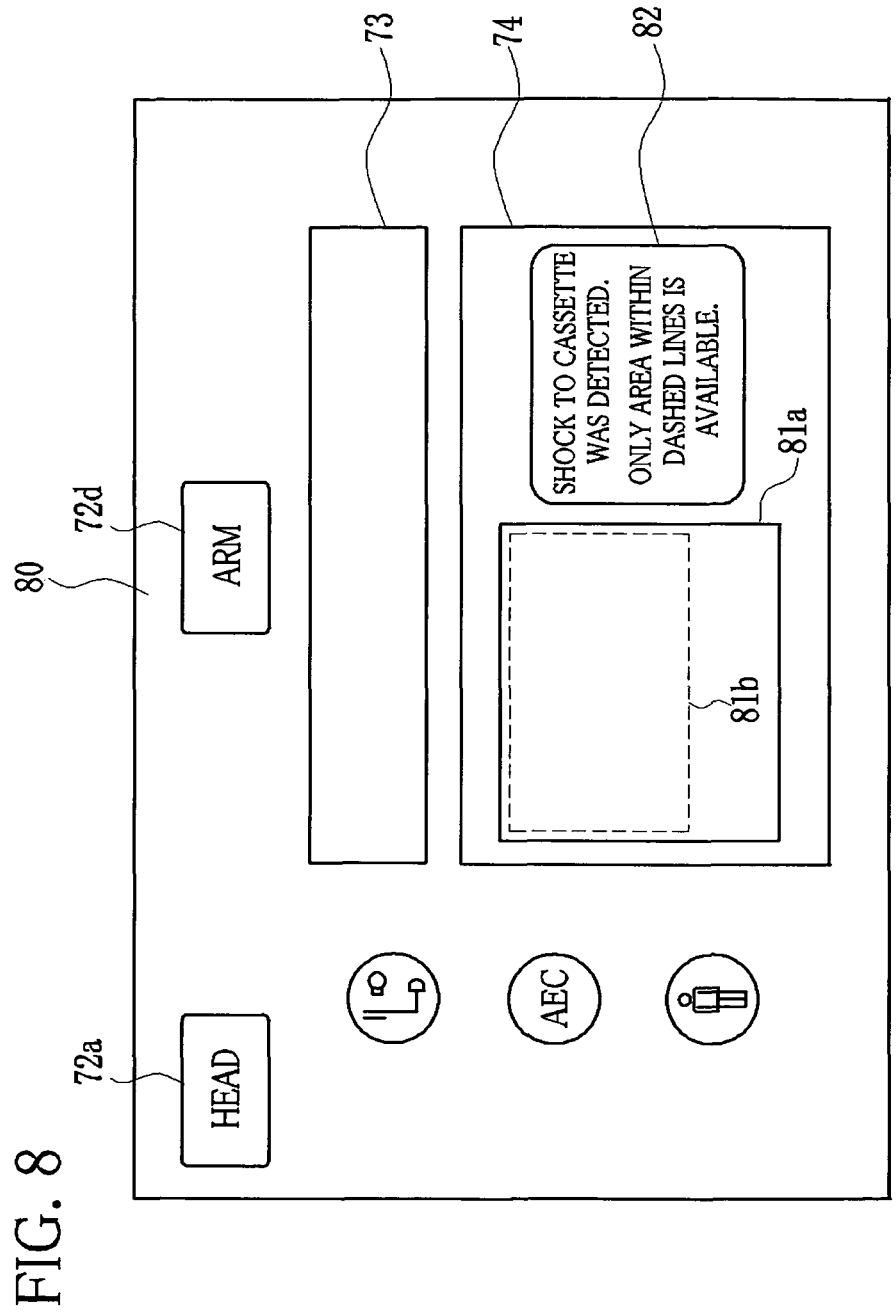
FIG. 8 is an explanatory view showing an example of a temporary imaging menu displayed on the monitor.

If the cassette 12 is judged to be partly available by the self diagnosis, the imaging menu management section 67 displays a temporary imaging menu 80 on the display unit 63, as shown in FIG. 8. In this temporary imaging menu 80, rectangular solid lines 81a representing the whole area of the X-ray detector 18 and rectangular broken lines 81b representing the usable area of the X-ray detector 18 within the whole area are displayed in the submenu box 74. In the submenu box 74, there is also displayed a message 82 saying the cassette 12 got a shock and only a part of the cassette 12 is available. Furthermore, only the choice buttons of the body parts to be examined where the damaged X-ray detector 18 can image, e.g. the choice buttons 72a and 72d of the head and the arm are displayed. The number and the types of the displayed choice buttons depend on the usable area of the X-ray detector 18.

The imaging condition management section 68 manages imaging conditions set up on the normal imaging menu 71 or the temporary imaging menu 80. The imaging conditions include, for example, the body part to be examined, an imaging method, and the number of X-ray images to be photographed, and are conditions on which a tube voltage, a tube current, an application time, and the like are determined to apply the X-ray beam of an appropriate dose to the body part to be examined.

Next, the operation of the X-ray imaging apparatus 10 will be described with referring to a flowchart of FIG. 9. If the cassette 12 is dropped or bumped during carriage, the shock detector 26 detects the acceleration or the shock (S1). A detection signal from the shock detector 26 is inputted to the cassette controller 51. In response to the detection signal from the shock detector 26, the cassette controller 51 makes the self diagnostic circuit 53 start the self diagnosis of the X-ray detector 18 (S2).

Figure 10:
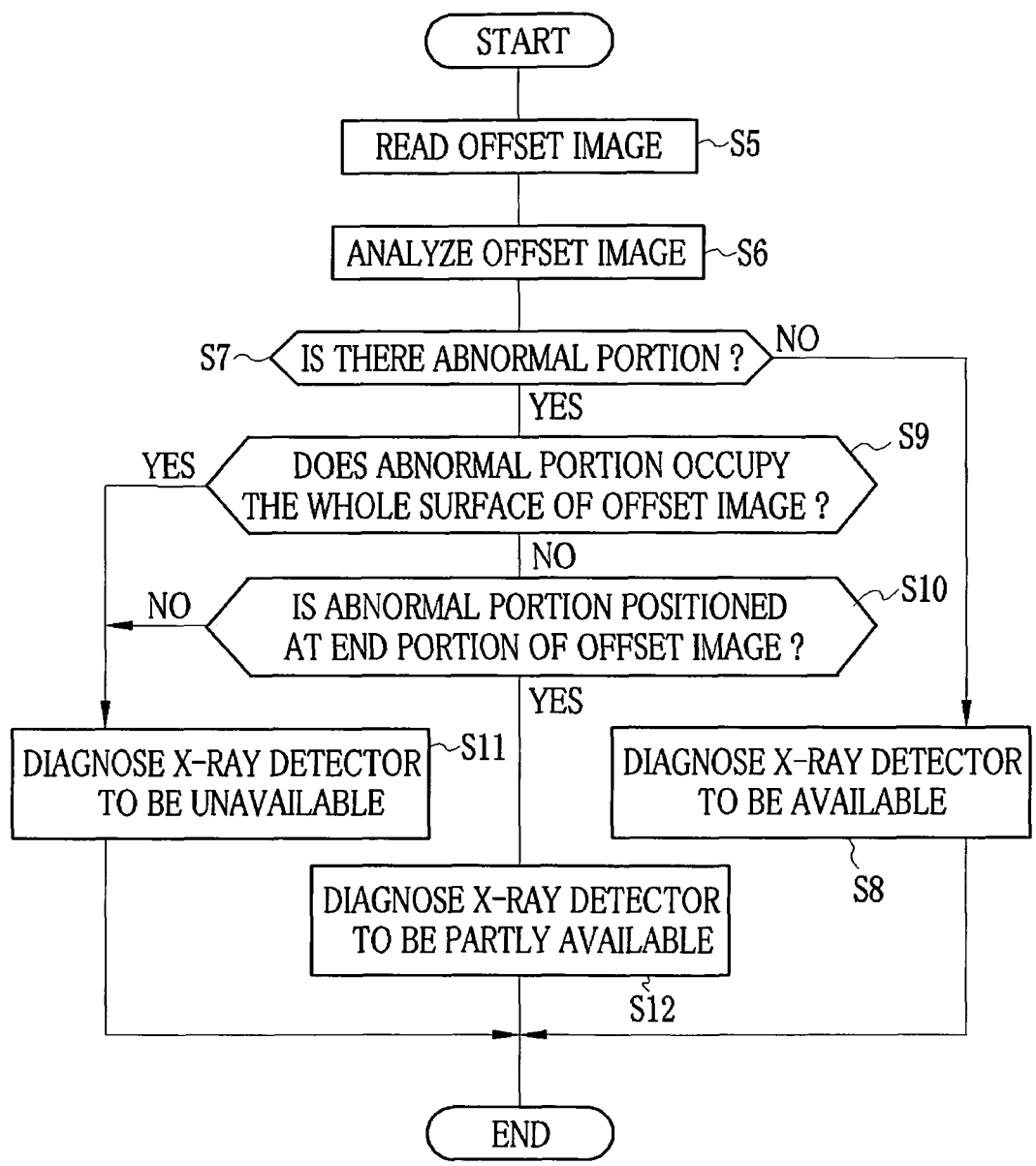
FIG. 10 is a flowchart of a self diagnosis.

FIG. 10 shows a flowchart of the self diagnosis (S2). The self diagnostic circuit 53 reads the offset image 56 from the X-ray detector 18 (S5), and analyzes at least one of the pixel value, the noise level, the point defect, and the line defect of the offset image 56 (S6). The self diagnostic circuit 53 determines the size and the position of the abnormal portion in the offset image (S7), and judges whether or not the X-ray detector 18 is available.

If there is no abnormal portion in the offset image 56 (NO in S7), the self diagnostic circuit 53 judges that the X-ray detector 18 is available (S8). If the abnormal portion occupies the whole surface of the offset image 56 (YES in S9), or the abnormal portion is positioned in the middle of the offset image 56 (NO in S10), the self diagnostic circuit 53 judges that the X-ray detector 18 is unavailable (S11). If the abnormal portion is positioned at the end portion of the offset image 56 (YES in S10), the self diagnostic circuit 53 judges that the X-ray detector 18 is partly available (S12).

Figure 9:
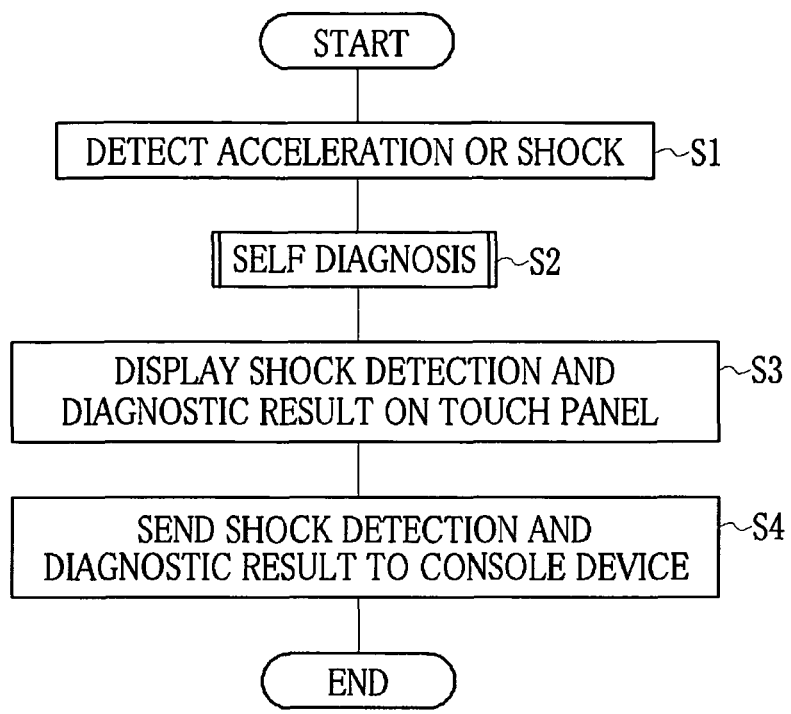
FIG. 9 is a flowchart in detecting acceleration or shock.

As shown in FIG. 9, the cassette controller 51 displays that the cassette 12 got the shock and the diagnostic result on the touch panel 25 (S3). Thus, a radiological technologist is immediately notified of a state of the cassette 12 during the carriage. The cassette controller 51 sends the shock detection and the diagnostic result to the console device 13 via the communication unit 24 (S4).

The console controller 59 stores the diagnostic result of the cassette 12 in the cassette information management section 66. The console controller 59 also displays the shock detection and the diagnostic result on the display unit 63, in order to call attention to the radiological technologist who is carrying out the radiography with use of the cassette 12.

In using the cassette 12, the console controller 59 reads the diagnostic result of the cassette 12 from the cassette information management section 66. If the cassette 12 is judged to be available, the imaging menu management section 67 displays on the display unit 63 the normal imaging menu 71 as shown in FIG. 6. If the cassette 12 is judged to be unavailable, the imaging menu management section 67 displays on the display unit 63 the message box 77 as shown in FIG. 7.

If the cassette 12 is judged to be partly available, the imaging menu management section 67 displays on the display unit 63 the temporary imaging menu 80 as shown in FIG. 8. Thus, even if the cassette 12 is partly damaged, the cassette 12 is temporarily usable for the radiography. In the temporary imaging menu 80, since the usable area of the X-ray detector 18 can be visually checked, the radiography is carried out with avoiding the use of a defective area of the X-ray detector 18. Furthermore, since only the choice buttons corresponding to the body parts that can be examined are displayed, the use of the defective area of the X-ray detector 18 is prevented.

Second to fourth embodiments of the present invention will be described below. The same reference numerals as those of the first embodiment indicate the same components as those of the first embodiment, and detailed description thereof will be omitted.

Second Embodiment

Figure 11:
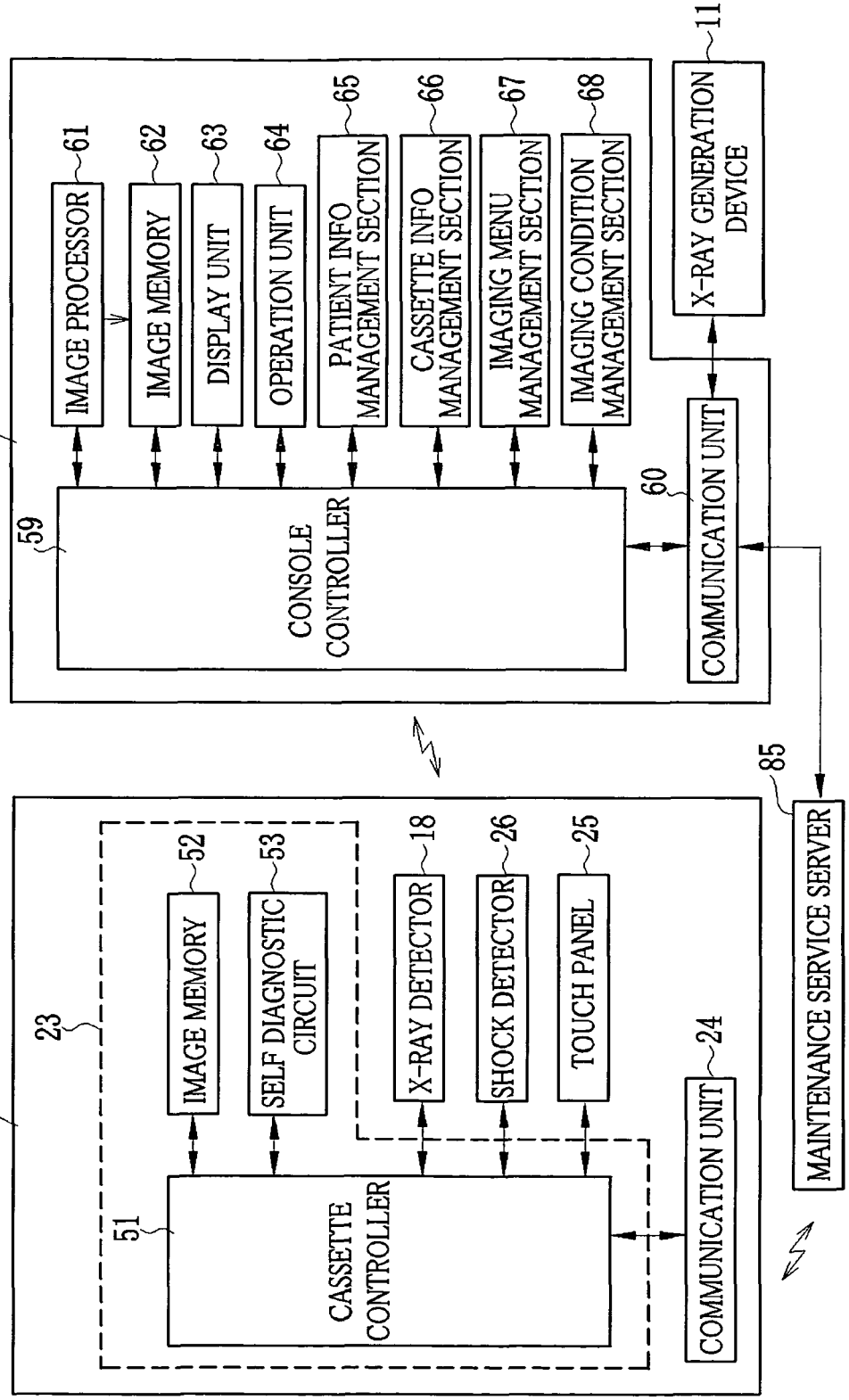
FIG. 11 is a block diagram of an X-ray imaging apparatus according to a second embodiment.

If the X-ray imaging apparatus uses a remote maintenance service including operation assistance and damage diagnosis, a maintenance service server of that service may carry out a diagnosis of the cassette 12. In an X-ray imaging apparatus 84 as shown in FIG. 11, the communication unit 60 of the console device 13 is connected to a maintenance service server 85 through a network. The communication unit 24 of the cassette 12 sends the shock detection and the offset image to the maintenance service server 85. The maintenance service server 85 analyzes the offset image with use of a CPU having higher performance than that of the cassette 12, and diagnoses whether or not the cassette 12 is available. The diagnostic result is sent to the cassette 12. Thus, the damage diagnosis is carried out more precisely and sophisticatedly.

In a case where the cassette 12 cannot be provided with a communication unit that is able to communicate with the maintenance service server 85, the shock detection and the offset image may be sent from the communication unit 60 of the console device 13. The cassette 12 or the console device 13 may automatically send the offset image and the like to the maintenance service server 85, whenever the shock is detected, or after use of the X-ray imaging apparatus 84 of the day.

Third Embodiment

In the first embodiment, the shock detection and the diagnostic result are displayed on the touch panel 25 and the consol device 13, when the shock detector 26 detects the shock. However, even though the cassette 12 is not damaged, the display of the shock detection and the diagnosis result is irksome, and may cause the cassette 12 to be mistaken for being damaged. Thus, if the self diagnosis circuit 53 judges that the cassette 12 is available, nothing is displayed except in a special case, while if the cassette 12 is judged to be unavailable, the shock detection and the diagnostic result are displayed on the touch panel 25 and the monitor of the console device 13.

Figure 12:
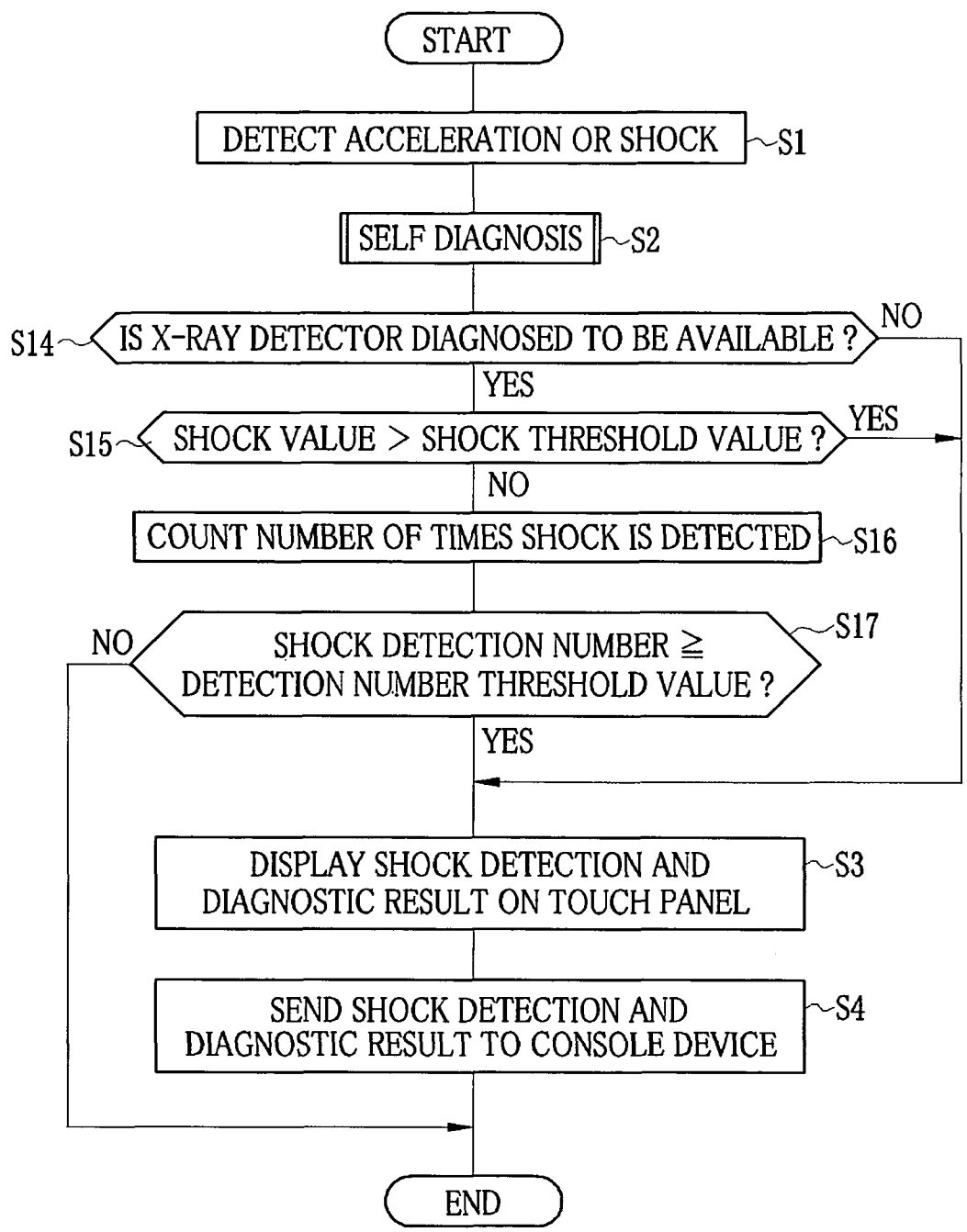
FIG. 12 is a flowchart in detecting acceleration or shock according to a third embodiment.

In the third embodiment, as shown in FIG. 12, when the cassette 12 is judged to be available (YES in S14), the cassette controller 51 of the cassette 12 compares a shock value measured by the shock detector 26 with a predetermined shock threshold value (S15). The shock threshold value is a magnitude of shock that may cause damage to the cassette 12. If the shock value is larger than the shock threshold value, the shock detection and the diagnostic result are displayed on the touch panel 25 (S3), and sent to the console device 13 (S4).

If the shock value is equal to or smaller than the shock threshold value, the cassette controller 51 counts the number of times the shock is detected (S16). When a shock detection number becomes equal to or exceeds a detection number threshold value, the shock detection and the diagnostic result are displayed on the touch panel 25 (S3), and sent to the consol device 13 (S4). The detection number threshold value is a number of counts from which the cassette 12 is likely to be damaged. The third embodiment can remove irksomeness due to the frequent display of the shock detection and the diagnostic result. When the possibility of damage of the cassette 12 is increased due to a significant magnitude of shock or a large number of shocks, the shock detection and the diagnostic result are displayed to call attention on the occurrence of damage.

Fourth Embodiment

Figure 13:
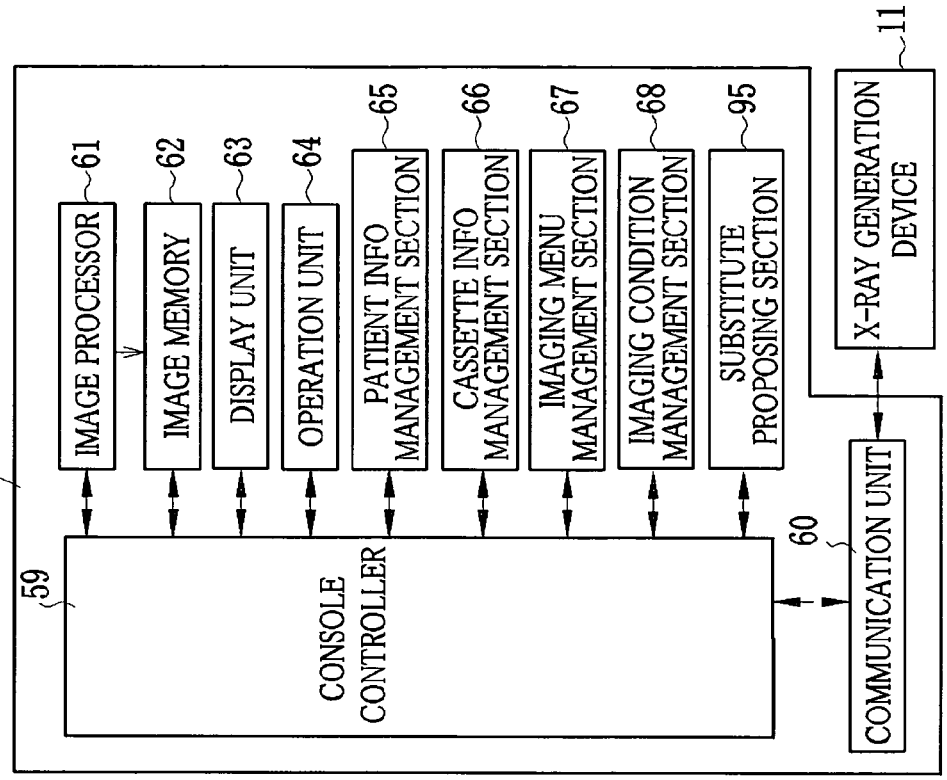
FIG. 13 is a block diagram of an X-ray imaging apparatus according to a fourth embodiment.

When the cassette 12 that was intended to be used has been damaged and become unavailable or partly available, a substitute cassette may be proposed. In an X-ray imaging apparatus 94 as shown in FIG. 13, the console device 13 is provided with a substitute proposing section 95. If the diagnostic result that says the cassette 12 is unavailable or partly available is sent from the cassette 12, the substitute proposing section 95 obtains information of another cassette registered on the console device 13 from the cassette information management section 66, and displays a message suggesting use of the substitute cassette on the display unit 63.

Therefore, the radiography is smoothly carried out even if the cassette 12 is damaged. The substitute cassette may be not only the cassette-type FPD but also an IP cassette or an X-ray film cassette. It is also preferable to notify the radiological technologist of a place where the substitute cassette is stored and the like.

In the above embodiments, if the X-ray beam is applied to the unusable area of the partly available X-ray detector 18, a warning message for suggesting reshooting may be issued. The present invention is not limited to the above first to fourth embodiments, and includes appropriate combinations of the first to fourth embodiments. In the above embodiments, an X-ray is took as an example of radiation, but other types of radiation including a γ-ray and an α-ray are available instead of the X-ray.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An x-ray radiation detection device comprising:
   an x-ray radiation detector having a plurality of pixels for converting an x-ray radiation into signal charges and accumulating the signal charges, the signal charges accumulated in the individual pixels during an entry of the x-ray radiation being read out as an image signal of a radiographic image;
   a shock detector for detecting a shock given to the x-ray radiation detector;
   a self diagnostic circuit for analyzing an offset image in response to detection of the shock by the shock detector to diagnose whether or not the x-ray radiation detector is available, the offset image being formed from the signal charges accumulated in the individual pixels of the x-ray radiation detector after the shock detection without the entry of the x-ray radiation; and
   a cassette casing for containing the x-ray radiation detector, the shock detector, and the self diagnostic circuit, wherein the self diagnostic circuit analyzes the offset image, and finds out an abnormal portion in the offset image, and diagnoses whether or not the x-ray radiation detector is available based on a size or a position of the abnormal portion.

2. The x-ray radiation detection device according to claim 1, wherein
   on condition that the offset image has no abnormal portion, the self diagnostic circuit diagnoses that the x-ray radiation detector is available;
   on condition that the abnormal portion occupies a whole surface of the offset image or is positioned in a middle of the offset image, the self diagnostic circuit diagnoses that the x-ray radiation detector is unavailable; and
   on condition that the abnormal portion is positioned at an end portion of the offset image, the self diagnostic circuit diagnoses that the x-ray radiation detector is partly available.

3. The x-ray radiation detection device according to claim 1, wherein the self diagnostic circuit analyzes at least one of a pixel value, a noise level, a point defect, and a line defect of the offset image.

4. The x-ray radiation detection device according to claim 3, further comprising:
   a display unit for displaying the shock detection and a diagnostic result.

5. The x-ray radiation detection device according to claim 4, wherein when the x-ray radiation detector is unavailable or partly available, the display unit carries out display operation, when a magnitude of the shock is a shock threshold value or more, or a number of times the shock is detected is a detection number threshold value or more.

6. The x-ray radiation detection device according to claim 3, further comprising:
   a sending unit for sending the shock detection and a diagnostic result, or the shock detection and the offset image to outside.

7. The x-ray radiation detection device according to claim 6, wherein when the x-ray radiation detector is unavailable or partly available, the sending unit carries out sending operation, when a magnitude of the shock is a shock threshold value or more, or a number of times the shock is detected is a detection number threshold value or more.

8. An x-ray radiation imaging system comprising:
   A. an x-ray radiation generation device for applying an x-ray radiation to an object;
   B. an x-ray radiation detection device including:
   an x-ray radiation detector having a plurality of pixels for converting the x-ray radiation into signal charges and accumulating the signal charges, the signal charges accumulated in the individual pixels during an entry of the x-ray radiation being read out as an image signal of a radiographic image;
   a shock detector for detecting a shock given to the x-ray radiation detector;
   a self diagnostic circuit for analyzing an offset image in response to detection of the shock by the shock detector to diagnose whether or not the x-ray radiation detector is available, the offset image being formed from the signal charges accumulated in the individual pixels of the x-ray radiation detector after the shock detection without the entry of the x-ray radiation; and
   a portable cassette casing for containing the x-ray radiation detector, the shock detector, and the self diagnostic circuit; and
   C. an imaging control device for controlling the x-ray radiation generation device and the x-ray radiation detection device;

wherein the self diagnostic circuit analyzes the offset image, and finds out an abnormal portion in the offset image, and diagnoses whether or not the x-ray radiation detector is available based on a size or a position of the abnormal portion.

9. The x-ray radiation imaging system according to claim 8, further comprising:
   a maintenance device including:
   a judgment function for precisely judging from the offset image whether or not the x-ray radiation detector is available; and
   a communication unit for sending the offset image and a judgment result to the x-ray radiation detection device or the imaging control device.

10. A self diagnostic method of an x-ray radiation detection device, the x-ray radiation detection device having a plurality of pixels for converting an x-ray radiation into signal charges and accumulating the signal charges, the signal charges accumulated in the individual pixels during an entry of the x-ray radiation being read out as a radiographic image, the self diagnostic method comprising the steps of:
   detecting a shock given to the x-ray radiation detection device;
   just after detection of the shock, reading out as an offset image the signal charges accumulated in the individual pixels of the x-ray radiation detection device without the entry of the x-ray radiation;
   analyzing the offset image and finding out an abnormal portion occurring in the offset image; and
   diagnosing whether or not the x-ray radiation detection device is available based on a size or a position of the abnormal portion.

11. The self diagnostic method according to claim 10, wherein in the diagnosing step,
   on condition that the offset image has no abnormal portion, the x-ray radiation detection device is diagnosed to be available;
   on condition that the abnormal portion occupies a whole surface of the offset image or is positioned in a middle of the offset image, the x-ray radiation detection device is diagnosed to be unavailable; and
   on condition that the abnormal portion is positioned at an end portion of the offset image, the x-ray radiation detection device is diagnosed to be partly available.

* * * * *